United States Patent [19]

Newman

[11] Patent Number: 5,167,238
[45] Date of Patent: Dec. 1, 1992

[54] FLUID SAMPLING DEVICE

[75] Inventor: David P. Newman, Arvada, Colo.

[73] Assignee: Cobe Laboratories, Inc., Lakewood, Colo.

[21] Appl. No.: 694,546

[22] Filed: May 2, 1991

[51] Int. Cl.⁵ ............................................. A61B 5/00
[52] U.S. Cl. ................................... 128/760; 604/236
[58] Field of Search .................. 128/760, 763–766, 128/770; 604/52, 181, 182, 229, 233, 236, 240, 246, 249

[56] References Cited

U.S. PATENT DOCUMENTS

| | | | |
|---|---|---|---|
| 3,143,109 | 8/1964 | Gewertz | 604/236 |
| 3,459,177 | 8/1969 | Dueschle . | |
| 3,557,778 | 1/1971 | Hughes . | |
| 3,570,484 | 3/1971 | Steer et al. . | |
| 3,957,052 | 5/1976 | Topham | 604/236 |
| 4,143,853 | 3/1979 | Abramson . | |
| 4,186,752 | 2/1980 | Guerra | 604/236 |
| 4,387,879 | 6/1983 | Tauschinski . | |
| 4,543,094 | 9/1985 | Barnell | 604/236 |
| 4,673,386 | 6/1987 | Gordon | 604/48 |
| 4,678,107 | 7/1987 | Ennis, III | 604/228 |
| 4,763,648 | 8/1988 | Wyatt | 128/762 |

Primary Examiner—Max Hindenburg

[57] ABSTRACT

A fluid sampling device in which a resilient element held between an actuator and a probe drives the tip of the latter sealingly against a source of fluid, and creates a negative pressure at the tip on its removal from the source.

6 Claims, 1 Drawing Sheet

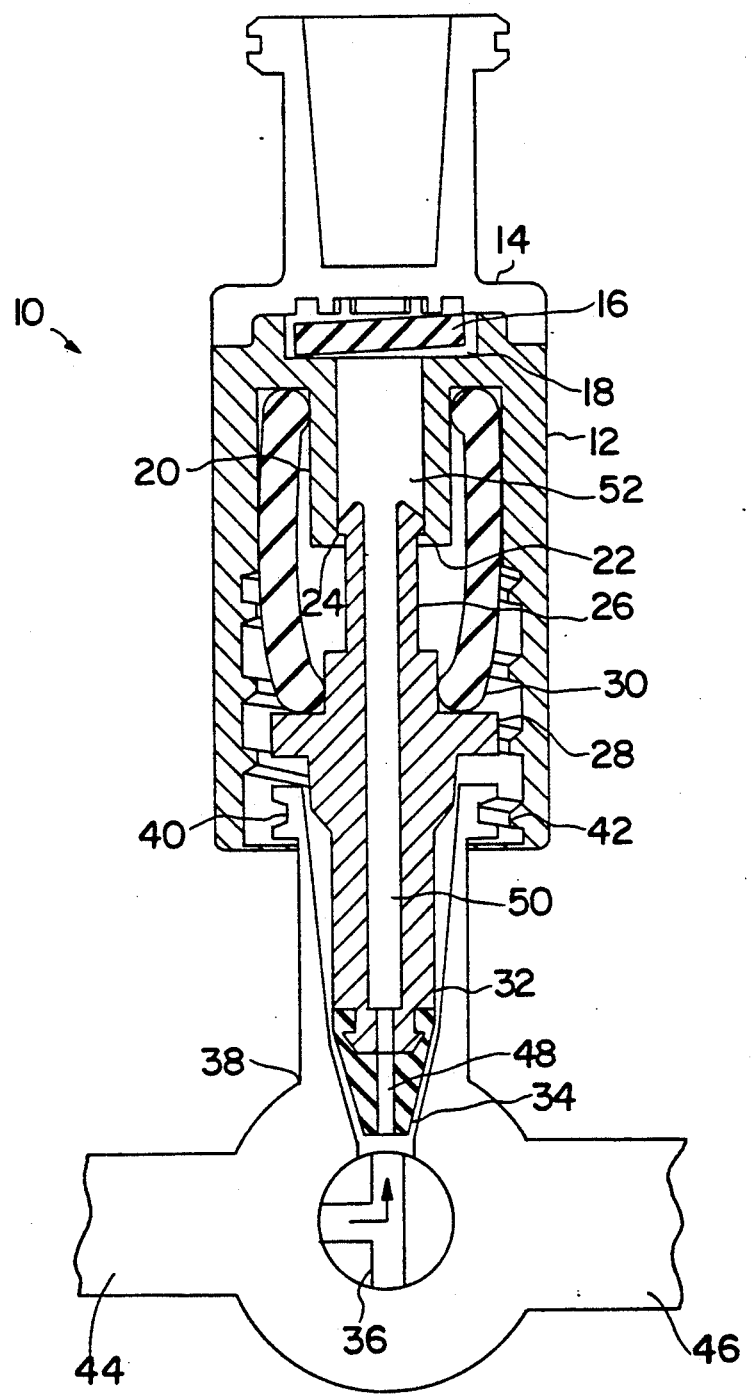

FLUID SAMPLING DEVICE

FIELD OF THE INVENTION

This invention relates to devices for sampling fluids, and more particularly for sampling blood flowing in a line with disengagement control.

BACKGROUND OF THE INVENTION

It is known in the art that the number of needle insertions is desirably minimized; and that valving may be used to permit a plurality of samples to be successively taken, with if desired different syringes, from one needle site. It is known that a stopcock can be used here to control flow. It is known too to incorporate a check valve in a blood specimen collection device, to prevent blood backflow into the patient. Use of an elastomerically receding member to create a negative pressure upon the end of dispensing from, for example, a syringe, to prevent undesirable fluid movement after the desired dispensing is known.

SUMMARY OF THE INVENTION

It has been discovered that repeated sampling, as from a single needle site, can be carried out, with simplicity, economy, freedom from septa and undue waveform compromise, and cleaning difficulties, if there is provided, with a valve for fluid, a probe to operatively engage the valve, and an actuator, a resilient member deformed by actuator movement to resiliently force the probe into operative engagement with the valve to sealingly engage the probe, and resuming its undeformed configuration upon reverse movement of the actuator, to produce a negative pressure at the probe tip.

In preferred embodiments, the resilient member is elastomeric and placed under compression in movement of a probe tip toward the valve; the probe tip is elastomeric and engages a stopcock valving portion; Luer male threads on a housing-actuator engage female Luer threads on a stopcock to move the probe toward the valve; there is a passage through the probe and housing to a check valve permitting flow only in a direction away from the stopcock; and a fitting with female Luer threads is provided just downstream of the check valve.

PREFERRED EMBODIMENT

Description of the preferred operation follows: drawing, structure, and operation.

DRAWING

There is shown in the drawing a side elevation of the preferred embodiment, partially in section, and partially diagrammatic.

STRUCTURE

The preferred embodiment is shown generally at 10.

Housing 12, of injection molded polycarbonate, is solvent-bonded to a female-threaded Luer connector 14, also of injection molded polycarbonate, and carries disk check valve 16 (of 0.040 inch thick Dow Corning Silastic medical grade sheeting) in deeper counterbore 18.

Depending from the counterbore 18 portion of housing 12 is probe engagement portion 20, also of injection molded polycarbonate, with inwardly directed rim 22 which engages rim 24 of probe 26.

Probe 26 includes ledge 28, an upper surface of which supports elastomeric barrel 30, and tip 32 which receives and carries elastomeric tip 34, selectively engageable with valving element 36 of stopcock 38, which is connected (by means not shown) to a blood flow line.

Barrel 30 is of compression-molded silicone sold by Lexington Medical, South Hill, S.C., under the designation "Dow 4-2483". It is 0.0400 inches in axial dimension, has an outside diameter of 0.275 inches, and a wall thickness through its main body of 0.040 inches.

The upper portion of stopcock 38 includes female Luer threads 40, which engage male threads 42 within housing 12.

OPERATION

In operation, blood is flowing through stopcock 38 from a single needle site, the stopcock valving portion 36 being rotated so that the two coaxial portions of the valving portion opening are aligned with stopcock flow path portions 44 and 46. The valving portion is then rotated to the position shown in the figure, and housing 12 rotated to axially compress barrel elastomeric portion 30, which in turn drives elastomeric tip 34 into sealing engagement with valving portion 36.

A syringe may then be engaged with the female thread of connector 14, and blood drawn through passage 48, 50, and 52 of probe tip 32, probe 26, and housing 12, through check valve 16, and (through a passage not shown) into Luer connector 14.

When housing 12 is rotated the other way, after rotating the stopcock valve portion for inline flow once more, barrel element 30 creates a negative pressure sealing check valve 16 and sucking back any blood contained in the probe tip passage 48.

Other embodiments within the claims will occur to those skilled in the art.

What is claimed is:

1. A fluid sampling device which comprises
   a probe for sealingly engaging a fluid container,
   an actuator for movement relative to said probe, and
   resilient means connected between said probe and said actuator,
   said resilient means being arranged
       to urge said probe against said fluid container when said actuator is moved in one direction, and
       to create a negative pressure when said actuator is moved in the opposite direction.
2. The device of claim 1 in which said resilient means is an elastomeric element-compressibly mounted between said actuator and said probe.
3. The device of claim 2 in which said resilient means is generally barrel shaped.
4. The device of claim 3 in which said resilient means has rims generally circular in cross-section, and of thickness greater than the remainder of the wall of said means.
5. The device of claim 2 in which said resilient means is held between a counterbore in said actuator and a ledge on said probe.
6. The device of claim, 1 in which said probe includes an elastomeric tip.

* * * * *